United States Patent [19]
Abdel-Monem et al.

[11] Patent Number: 5,430,164
[45] Date of Patent: Jul. 4, 1995

[54] ENHANCED SOLUBILIZATION OF ZINC AND MANGANESE METHIONINE COMPLEX SALTS BY ADDITION OF FERRIC ION

[75] Inventors: Mahmoud M. Abdel-Monem, Moscow, Id.; Michael D. Anderson, Minnetonka, Minn.

[73] Assignee: Zinpro Corporation, Edina, Minn.

[21] Appl. No.: 324,881

[22] Filed: Oct. 18, 1994

[51] Int. Cl.6 .......................... C07F 13/00; C07F 3/06
[52] U.S. Cl. .......................................... 556/2; 556/50; 556/134
[58] Field of Search ............... 556/2, 50, 134

[56] References Cited

U.S. PATENT DOCUMENTS

| | | | |
|---|---|---|---|
| 3,463,858 | 8/1969 | Anderson | 424/289 |
| 3,925,433 | 12/1975 | Abdel-Monem et al. | 260/438.5 R |
| 3,941,818 | 3/1976 | Abdel-Monem | 260/429.9 |
| 3,950,372 | 4/1976 | Abdel-Monem | 260/429 R |
| 4,021,569 | 5/1977 | Abdel-Monem | 424/289 |
| 4,039,681 | 8/1977 | Abdel-Monem | 424/289 |
| 4,067,994 | 1/1978 | Anderson et al. | 424/295 |
| 4,670,269 | 6/1987 | Abdel-Monem | 426/74 |
| 4,678,854 | 7/1987 | Abdel-Monem | 556/149 |
| 4,764,633 | 8/1988 | Anderson et al. | 556/50 |
| 4,900,561 | 2/1990 | Abdel-Monem et al. | 426/2 |
| 4,948,594 | 8/1990 | Abdel-Monem et al. | 426/2 |
| 4,956,188 | 9/1990 | Anderson | 426/74 |
| 5,061,815 | 10/1991 | Leu | 556/118 |
| 5,278,329 | 1/1994 | Anderson | 556/50 |

*Primary Examiner*—José G. Dees
*Assistant Examiner*—Porfirio Nazario-Gonzalez
*Attorney, Agent, or Firm*—Zarley, McKee, Thomte, Voorhees, & Sease

[57] ABSTRACT

Method of enhancing the water solubility of dry zinc methionine complex salts by reacting in water soluble zinc salt with mentionine in the presence of ferric ion with the amount being between about 15 mole percent and 30 mole percent of the amount of zinc present.

4 Claims, No Drawings

ENHANCED SOLUBILIZATION OF ZINC AND MANGANESE METHIONINE COMPLEX SALTS BY ADDITION OF FERRIC ION

BACKGROUND OF THE INVENTION

This invention relates to an improvement in the properties of dry powder complexes of zinc and manganese with methionine in the 1:1 ratio. In that sense it represents a significant improvement over the process disclosed in commonly owned U.S. Pat. No. 4,764,633, and as well, over commonly owned and now expired U.S. Pat. No. 3,941,818 issued Mar. 2, 1976 entitled "1:1 ZINC METHIONINE COMPLEXES", and U.S. Letters Pat. No. 3,950,372 issued Apr. 13, 1976, and entitled "1:1 MANGANESE ALPHA AMINO ACID COMPLEXES". Thus U.S. Pat. No. 3,941,818 and U.S. Pat. No. 3,950,372 relate to 1:1 complexed salts per se of zinc and manganese with the amino acid methionine. These salts, as identified in the earlier patents, have the useful feature of being highly body absorbable nutritional supplements for animals that provide readily available sources of zinc and manganese on the one hand, and the essential amino acid methionine on the other.

The common assignee of both of these patents makes a variety of transition metal complexes with alpha amino acids for sale. For example, see U.S. Pat. No. 5,061,815 relating to metal lysine complexes and methods for producing metal lysine complexes, as well as U.S. Pat. No. 5,278,329 for L-form 1:1 metal methionine complexes.

Complexes of lysine are very easily soluble in water. However, complexes of metals such as zinc and manganese and methionine are less soluble in water than the complexes of metals and lysine.

In Anderson, U.S. Pat. No. 4,764,633, an improvement in the complexing process is disclosed wherein the complexing of either zinc or manganese ions with methionine is conducted in the presence of a catalytically effective amount of ferric ion. The amount of ferric ion described is about 2% to about 10% based on the dry weight basis of the methionine, preferably from about 4% to about 8% based on the dry weight basis of the methionine.

For effective feed supplements, the supplement must be in a powdered, dry form, and it must be readily soluble in the gut of animals; otherwise, much of the supplement will not be absorbed into the blood stream. It also is useful to have water soluble supplements so that the user may administer them through aqueous systems.

While U.S. Pat. No. 4,764,633 enhances the amount of complexation, it does not enhance the solubility of the final dry product.

Accordingly, there has been a real and a continuing need for the discovery of a process which will enhance the solubility characteristics of the dry 1:1 complexes of zinc and manganese with methionine.

This invention has as its primary objective the fulfillment of this need in order that dry 1:1 manganese methionine complexes and dry 1:1 zinc methionine complexes have enhanced solubility in comparison with those prepared as described in U.S. Pat. No. 3,941,818 and U.S. Pat. No. 3,950,372.

For details of the desirability and the utility of 1:1 manganese methionine complexes, see the previously referred to U.S. Pat. No. 3,950,372 which is incorporated herein by reference. For details of the desirability and the utility of 1:1 zinc methionine complexes, see U.S. Pat. No. 3,941,818, which is incorporated herein by reference.

The method of accomplishing each of the above objectives of this invention will become apparent from the detailed description of the invention which follows hereinafter.

SUMMARY OF THE INVENTION

Method of enhancing the water solubility of dry zinc methionine complex salts by reacting in water soluble zinc salt with methionine in the presence of ferric ion with the amount being between 15 mole percent and 30 mole percent of the amount of zinc present.

DETAILED DESCRIPTION OF THE INVENTION

It is important to note that the respective zinc and manganese compounds which are prepared in accordance with this invention are referred to as complexed salts. These salts are to be carefully distinguished from conventional salts such as, for example, zinc chloride or manganese chloride. Such conventional salts such as zinc chloride or manganese chloride contain only an electrostatic attraction between the cation and the anion. The 1:1 complexed salts prepared by this invention differ from conventional salts in that while they have an electrostatic attraction between the cation and the anion, there is also a coordination bond between the cation and the amino moiety of the alpha amino acid.

With regard to the zinc methionine complexed salts which are prepared in accordance with the improved process of this invention, they have the general formula:

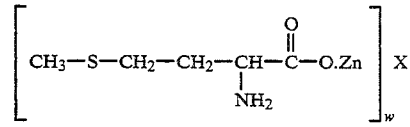

wherein X is an anion and w is an integer equal to the anionic charge of X. The cation of these complexed salts is represented by the bracketed material in the above formula and represents a 1:1 complex of zinc and methionine.

With regard to the manganese alpha amino acid complex salts of the present invention, they have the formula:

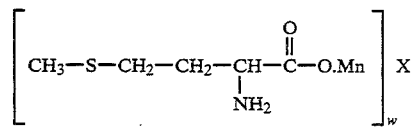

X and w are as previously defined.

The process of preparing the desired zinc and methionine 1:1 complex salts of methionine as referred to herein is straightforward and direct. Commonly it begins with the use of a water soluble zinc salt and/or a water soluble manganese salt, respectively. Suitable zinc salts which can be employed are the halides, the sulfates, and the phosphates. The desired molar ratio of zinc salt to methionine is 1:1. Suitable manganese salts which can be employed are likewise halides, sulfates and phosphates. The desired molar ratio of manganese to methionine is 1:1. In each instance, the sulfate salts are preferred from the standpoint of availability and, at least currently, cost.

In the general process, these salts are at least partially water dissolved, preferably at elevated temperatures. Temperatures within the range of from about 180° F. to about 205° F. have been found desirable, most preferably temperatures within the range of 190° F. to about 205° F. In actual practice, one common technique is to stir the salt into a water solution while simultaneously injecting steam to elevate the temperature within the desired range.

In accordance with the process of our prior patent, U.S. Pat. No. 4,764,633, along with these reactants, a catalytically effective amount of ferric ion is added to enhance complexation yield. The amount added is from about 2% to about 10% based upon the dry weight of methionine. The earlier patent teaches that levels above the 10 molar percent level based upon the dry weight of methionine should be avoided. This corresponds to the same molar percentages for zinc, i.e. 2% to 10%, and preferably 4% to 8%. As previously mentioned in the earlier patent, it was discovered that when percentages of ferric ion are added to the reactants at the levels there specified, desirable things occur. In the first instance, the dissolving of the salt and the amino acid in the water appears to be significantly enhanced, and in the second instance there is an increased yield of the desirable 1:1 complexes formed. That earlier discovery, however, involved formation of the reactants and did not involve solving the problems that zinc and manganese methionine complexes are inherently difficultly soluble at best after formation.

It has now been surprisingly discovered that if substantially increased amounts of ferric ion are added during the formation reaction for the complexes, not only does one get a substantially increased yield of the desirable 1:1 complexes, but in addition the dry product produced by the process is more soluble, and the solution produced is more stable.

For purposes of this invention, the amount of dry weight molar basis based upon the mole weight of zinc or manganese should be from about 15% to about 30% on a mole weight basis. Preferably the amount is within the range of from 15% to 20%. As evidenced by the examples, the amount appears to be critical in order to achieve the desired solubility of the dry weight product. In other words, the enhanced solubility phenomena of the present invention is not achieved until the level of ferric ion salt added is about 15%. Thus the levels expressed in U.S. Pat. No. 4,764,633 are too low to provide the observed enhanced solubility phenomena of the present invention.

While not wishing to be bound by any theory of operability, it is believed that the presence of the ferric ion., along with the manganese or the zinc ion and methionine, brings about an equilibrium between ferric methionine complexes and those of zinc and manganese. Since the ferric ion complexes formed are much more soluble than either the zinc or the manganese complexes, the equilibrium that occurs seems to shift the equilibrium in the reaction of the zinc and the methionine to provide a far more soluble product. In any event, the important fact is not theoretically how the reaction works, but that it does simply work to provide a product of significantly enhanced solubility.

The ferric ion which is added may be in the form of any water soluble salt such as ferric chloride, ferric sulfate, ferric phosphate, ferric acitate, or any other suitable water soluble ferric salt. The most preferred, however, is ferric chloride and ferric sulfate.

The following examples are offered to further illustrate the improved process of the present invention and the critical levels of ferric ion required to achieve the enhanced solubility of the dry products prepared.

EXAMPLES OF ZINC METHIONINE ACID SULFATE SOLUBILIZATION BY FERRIC CHLORIDE

The addition of ferric chloride was found to enhance the solubility of zinc methionine acid sulfate. However, the concentration of ferric chloride required to produce a readily soluble and stable material is critical. The following experiment was conducted to determine the optimum concentration of ferric chloride.

Seven samples of zinc methionine acid sulfate containing variable concentrations of $FeCl_3$ were prepared. Zinc sulfate heptahydrate ($ZnSO_6.7H_2O$; 14.38$_g$; 0.05 mole) was dissolved in 30 mL of distilled water in a 250 mL beaker. DL-Methionine (7.46 g, 0.05 mole) was added. The mixture was heated to boiling, and the heating continued for an additional 10 minutes.

Ferric chloride hexahydrate ($FeCl_3.6H_2O$, 13.52$_g$; 0.05 mole) was transferred into a 100 mL volumetric flask. The solid was dissolved in approximately 50 mL of $H_2O$. Water was added to volume.

Using a 50 mL burret, a specific volume of the ferric chloride solution was added to each of the boiling solutions of zinc methionine acid sulfate (Table 1). Each solution was evaporated to dryness under reduced pressure at 70° C. using a rotary evaporator. A sample (1.0 g) of each of the dried products was transferred into a stoppered test tube. Distilled water was added in 0.5 mL increments and thoroughly mixed. The volume required for complete solubilization of the sample is reported in Table 2.

TABLE 1

| Sample No. | Zinc Sulfate wt. g. | Zinc Sulfate mole | DL-Methionine wt. g. | DL-Methionine mole | Ferric Chloride Solution (mL) | Ferric Chloride mole | Fe/Zn mole % |
|---|---|---|---|---|---|---|---|
| 1 | 14.3% | 0.05 | 7.46 | 0.05 | 5 | 0.0025 | 5 |
| 2 | 14.3% | 0.05 | 7.46 | 0.05 | 7 | 0.0035 | 7 |
| 3 | 14.3% | 0.05 | 7.46 | 0.05 | 9 | 0.0045 | 9 |
| 4 | 14.3% | 0.05 | 7.46 | 0.05 | 11 | 0.0055 | 11 |
| 5 | 14.3% | 0.05 | 7.46 | 0.05 | 13 | 0.0065 | 13 |
| 6 | 14.3% | 0.05 | 7.46 | 0.05 | 15 | 0.0075 | 15 |
| 7 | 14.3% | 0.05 | 7.46 | 0.05 | 17 | 0.0085 | 17 |

TABLE 2

| | Fe/Zn Molar % | $FeCl_3$/Methionine w/w % | Vol. of Water to Dissolve 1 g Sample (mL) | Solubility g/mL |
|---|---|---|---|---|
| 1 | 5 | 5.44 | 12.5 | 0.08* |
| 2 | 7 | 7.62 | 12.5 | 0.08* |
| 3 | 9 | 9.80 | 11.0 | 0.09* |
| 4 | 11 | 11.97 | 10.5 | 0.10* |
| 5 | 13 | 14.15 | 9.5 | 0.11* |
| 6 | 15 | 16.33 | 2.5 | 0.40 |
| 7 | 17 | 18.51 | 2.0 | 0.50 |

*Solution was unstable. A white ppt of Methionine was formed upon standing.

From the above Table 1 and Table 2 it can be seen that a critical limit occurs with the demarcation line between 13 molar percent and 15 molar percent. In practice with other experiments (not specifically shown here), it seems that only a little increased value is obtained in going beyond 15%. In other words, the increased solubility does not significantly improve, even though the level might go up to as much as 30%. Thus, about 15% appears to be the critical distinction and 30% is a practical and economic upper limit.

What is claimed is:

1. A method of enhancing the water solubility of dry methionine complex salts of the metals zinc and/or manganese, said method comprising:

reacting a water soluble metal salt with the metal being selected from the group consisting of zinc and manganese salts with methionine in the presence of ferric ion, the amount of ferric ion is within the range of from about 15 molar percent to about 30 molar percent of the amount of metal salt present.

2. The process of claim 1 wherein the metal is zinc.

3. The process of claim 1 wherein the metal is manganese.

4. The process of claim 1 wherein the amount of ferric ion is within the range of from about 15 molar percent to about 20 molar percent of the amount of metal salt present.

* * * * *